US011555024B2

(12) United States Patent
Miyauchi et al.

(10) Patent No.: US 11,555,024 B2
(45) Date of Patent: Jan. 17, 2023

(54) ALDEHYDE ADDUCT OF HEXAFLUOROPROPYLENE OXIDE, METHOD OF MANUFACTURING TRIFLUOROPYRUVYL FLUORIDE DIMER AND METHOD OF MANUFACTURING PERFLUORO(2,4-DIMETHYL-2-FLUOROFORMYL-1,3-DIOXOLANE)

(71) Applicants: TOSOH CORPORATION, Shunan (JP); TOSOH FINECHEM CORPORATION, Shunan (JP)

(72) Inventors: Hideki Miyauchi, Shunan (JP); Hiroshi Matsuo, Shunan (JP); Takumi Kagawa, Shunan (JP); Norihisa Kondo, Shunan (JP); Hideyuki Mimura, Shunan (JP)

(73) Assignees: TOSOH CORPORATION, Shunan (JP); TOSOH FINECHEM CORPORATION, Shunan (JP)

( * ) Notice: Subject to any disclaimer, the term of this patent is extended or adjusted under 35 U.S.C. 154(b) by 0 days.

(21) Appl. No.: 17/272,817

(22) PCT Filed: Sep. 3, 2019

(86) PCT No.: PCT/JP2019/034569
§ 371 (c)(1),
(2) Date: Mar. 2, 2021

(87) PCT Pub. No.: WO2020/050249
PCT Pub. Date: Mar. 12, 2020

(65) Prior Publication Data
US 2021/0214332 A1 Jul. 15, 2021

(30) Foreign Application Priority Data

Sep. 3, 2018 (JP) .............................. JP2018-164730
Apr. 26, 2019 (JP) .............................. JP2019-086628
Apr. 26, 2019 (JP) .............................. JP2019-086640

(51) Int. Cl.
*C07D 317/42* (2006.01)
*C07C 45/58* (2006.01)

(52) U.S. Cl.
CPC ............ *C07D 317/42* (2013.01); *C07C 45/58* (2013.01)

(58) Field of Classification Search
CPC .................................................. C07D 317/42
USPC ...................................................... 260/340.2
See application file for complete search history.

(56) References Cited

U.S. PATENT DOCUMENTS 3,308,107 A 3/1967 Selman
3,321,517 A 5/1967 Selman
3,404,162 A 10/1968 Selman
3,450,716 A 6/1969 Selman
3,467,702 A 9/1969 Selman
3,475,456 A 10/1969 Selman
3,962,279 A 6/1976 England
4,287,124 A * 9/1981 Siegemund .......... C07D 317/42
549/455
4,420,638 A 12/1983 Uschold
4,474,998 A 10/1984 Uschold
2014/0018414 A1 1/2014 Brosnan
2015/0157596 A1 6/2015 Brosnan

FOREIGN PATENT DOCUMENTS

FR 1.422.169 A 10/1964
GB 1051647 A 12/1966
JP 52-142072 A 11/1977
JP 55-113775 A 9/1980
JP 58-180449 A 10/1983
JP 2015-525757 A 9/2015
WO WO 2014/011235 A1 1/2014

OTHER PUBLICATIONS

Greco "Comprehensive Organic Chemistry Experiments for the Laboratory Classroom" 2017 translated from 2011 Portuguese language edition, edited by Carlos A M Afonso, RSC publishing, p. 61.*
Henze "The Number of Structurally Isomeric Alcohols of the Methanol Series" Journal of the American Chemical Society 1931, 3042.*
International Search Report dated Nov. 19, 2019 in PCT/JP2019/034569 (submitting English translation only), 6 pages.
Frantisek Mikes, et al., Synthesis and Characterization of an Amorphous Perfluoropolymer: Poly(perfluoro-2-methylene-4-methyl-1,3-dioxolane) Macromolecules, vol. 38, No. 10, 2005, pp. 4237-4245.
Yuminov, V. S. et al., "Perfluorinated Dioxolanes. 1. Synthesis of perfluoro-4-oxo-1,3-Dioxolane Derivatives, Izvestiya Akademii NaukSSSR", Seriya Khimicheskaya, No. 2, 1988, pp. 392-395.
Herbert Muffler, et al., "Cyclization in the Presence of Fluoride Ions. 2. 4, 5-Perfluoro-1, 3-Dioxolanes" Journal of Fluorine Chemistry, vol. 21, No. 2, 1982, pp. 107-132.
International Search Report and Written Opinion of the International Searching Authority dated Nov. 19, 2019 in PCT/JP2019/034569, 15 pages (English translation of the International Search Report previously filed).
International Preliminary Report on Patentability dated Mar. 18, 2021 in PCT/JP2019/034569 (with English translation), 23 pages.
Takashi Ishihara, et al., "α-Pentafluoropropionylation of Ketones and Aldehydes using Hexafluoropropene Oxide. A Facile Synthesis of Fluorinated 1,3-Diketones" Bulletin of the Chemical Society of Japan, vol. 55, No. 10, 1982, pp. 3345-3346.
Extended European Search Report dated May 2, 2022 issued in European patent application No. 19857567.2.—8 pages.

* cited by examiner

*Primary Examiner* — David K O'Dell
(74) *Attorney, Agent, or Firm* — Oblon, McClelland, Maier & Neustadt, L.L.P.

(57) ABSTRACT

Provided is a method of manufacturing a trifluoropyruvyl fluoride dimer, including a reaction step of reacting hexafluoropropylene oxide and aldehyde.

9 Claims, No Drawings

ALDEHYDE ADDUCT OF HEXAFLUOROPROPYLENE OXIDE, METHOD OF MANUFACTURING TRIFLUOROPYRUVYL FLUORIDE DIMER AND METHOD OF MANUFACTURING PERFLUORO(2,4-DIMETHYL-2-FLUOROFORMYL-1,3-DIOXOLANE)

CROSS-REFERENCE TO RELATED APPLICATIONS

The present application is a 35 U.S.C. § 371 national stage patent application of International patent application PCT/JP2019/034569, filed on Sep. 3, 2019, which is based on and claims the benefits of priority to Japanese Application No. 2018-164730, filed on Sep. 3, 2018, Japanese Application No. 2019-086628, filed on Apr. 26, 2019, and Japanese Application No. 2019-086640, filed on Apr. 26, 2019. The entire contents of these applications are incorporated herein by reference.

TECHNICAL FIELD

The present invention relates to an aldehyde adduct of hexafluoropropylene oxide, a method of manufacturing a trifluoropyruvyl fluoride dimer, and a method of manufacturing perfluoro(2,4-dimethyl-2-fluoroformyl-1,3-dioxolane).

BACKGROUND ART

As a method of manufacturing a trifluoropyruvyl fluoride dimer, PTL 1 discloses a manufacturing method that involves reacting benzophenone and hexafluoropropylene oxide in an autoclave at 185° C. for 4 hours.

As a method of manufacturing perfluoro(2,4-dimethyl-2-fluoroformyl-1,3-dioxolane), PTL 2 discloses a method in which trifluoropyruvyl fluoride, which is used as a starting material, is reacted with hexafluoropropylene oxide in a diethylene glycol dimethyl ether solvent, in the presence of cesium fluoride.
[PTL 1] Specification of U.K. Patent No. 1051647
[PTL 2] Specification of U.S. Pat. No. 3,308,107

SUMMARY OF INVENTION

As a method of manufacturing trifluoropyruvyl fluoride (i.e. a monomer), PTL 1 discloses a method that is carried out in a normal-pressure flow system. Trifluoropyruvyl fluoride has a low boiling point, 9° C. to 10° C., and is thus difficult to handle industrially, whereas the trifluoropyruvyl fluoride dimer has a boiling point of 72° C. and is therefore easy to handle. However, the method of manufacturing a trifluoropyruvyl fluoride dimer disclosed in PTL 1 involves raising pressure to 4 MPa to 5 MPa, which necessitates an apparatus suitable for high-pressure reactions.

In view of the above, one aspect of the present invention provides for a method of manufacturing a trifluoropyruvyl fluoride dimer that can be carried out under mild conditions.

Another one aspect of the present invention provides for a manufacturing method that allows manufacturing perfluoro(2,4-dimethyl-2-fluoroformyl-1,3-dioxolane) with good yield by using, as a starting material, a trifluoropyruvyl fluoride dimer synthesized by the above manufacturing method.

As a result of extensive research concerning methods of manufacturing a trifluoropyruvyl fluoride dimer, the present inventors newly found that by using aldehyde instead of benzophenone, which is utilized in the manufacturing method disclosed in PTL 1, aldehyde adduct resulting from addition of aldehyde to hexafluoropropylene oxide can be prepared, and by further conducting the reaction, it becomes possible to manufacture a trifluoropyruvyl fluoride dimer under mild conditions.

The present inventors newly found out, moreover, that perfluoro(2,4-dimethyl-2-fluoroformyl-1,3-dioxolane) can be manufactured with good yield by using, as a starting material, the trifluoropyruvyl fluoride dimer obtained by the above method.

That is, the present invention is as follows.

[1] A method of manufacturing a trifluoropyruvyl fluoride dimer, including a reaction step of reacting hexafluoropropylene oxide and aldehyde.

[2] The method of manufacturing a trifluoropyruvyl fluoride dimer according to [1], wherein the hexafluoropropylene oxide and the aldehyde are reacted at 0° C. to 100° C. in the reaction step.

[3] The method of manufacturing a trifluoropyruvyl fluoride dimer according to [1] or [2], including an aging step of aging at equal to or higher than 100° C., after the reaction step.

[4] The method of manufacturing a trifluoropyruvyl fluoride dimer according to any of [1] to [3], including an aging step of aging at 100° C. to 150° C., after the reaction step.

[5] The method of manufacturing a trifluoropyruvyl fluoride dimer according to any of [1] to [4], wherein the aldehyde is aldehyde having no hydrogen atom at the α-position of the carbonyl group.

[6] The method of manufacturing a trifluoropyruvyl fluoride dimer according to any of [1] to [5], wherein the aldehyde is aromatic aldehyde.

[7] The method of manufacturing a trifluoropyruvyl fluoride dimer according to any of [1] to [6], wherein the aldehyde is electron donating group-substituted aromatic aldehyde.

[8] The method of manufacturing a trifluoropyruvyl fluoride dimer according to any of [1] to [7], wherein the aldehyde is electron donating group-substituted benzaldehyde.

[9] The method of manufacturing a trifluoropyruvyl fluoride dimer according to any of [1] to [8], wherein the aldehyde is 4-methoxybenzaldehyde.

[10] The method of manufacturing a trifluoropyruvyl fluoride dimer according to any of [1] to [9], wherein the reaction step is carried out at equal to or lower than 3.5 MPa.

[11] An aldehyde adduct in which aldehyde is added to hexafluoropropylene oxide, the aldehyde adduct being prepared by reacting hexafluoropropylene oxide and aldehyde.

[12] An aldehyde adduct being at least one selected from the group consisting of the aldehyde adduct represented by Formula 1, the aldehyde adduct represented by Formula 2 and the aldehyde adduct represented by Formula 3.

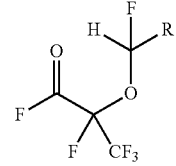

Formula 1

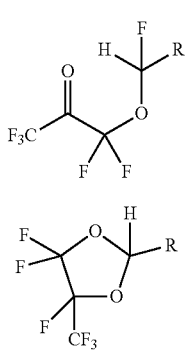

Formula 2

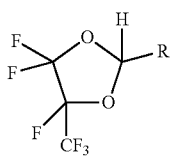

Formula 3

(In the formulae, R represents a substituted or unsubstituted alkyl group or aryl group.)

[13] A method of manufacturing perfluoro(2,4-dimethyl-2-fluoroformyl-1,3-dioxolane), the method having: a dimer synthesis step of synthesizing a trifluoropyruvyl fluoride dimer by the method according to any of [1] to [10]; and a dimer reaction step of allowing the synthesized trifluoropyruvyl fluoride dimer to react.

[14] The method of manufacturing perfluoro(2,4-dimethyl-2-fluoroformyl-1,3-dioxolane) according to [13], wherein the dimer reaction step is a step of allowing the trifluoropyruvyl fluoride dimer and hexafluoropropylene oxide to react in the presence of a fluoride, in an organic solvent.

[15] The method of manufacturing perfluoro(2,4-dimethyl-2-fluoroformyl-1,3-dioxolane) according to [13] or [14], including an isomerization step after the dimer reaction step.

[16] The method of manufacturing perfluoro(2,4-dimethyl-2-fluoroformyl-1,3-dioxolane) according to any of [13] to [15], wherein both layers of a reaction solution that separates into two layers and is obtained by the method according to any of [1] to [10] are subjected to the dimer reaction step.

According to one aspect of the present invention, a more industrial method of manufacturing a trifluoropyruvyl fluoride dimer, that can be carried out in general-purpose equipment can be provided.

According to one aspect of the present invention, a manufacturing method can be provided that allows manufacturing perfluoro(2,4-dimethyl-2-fluoroformyl-1,3-dioxolane) with good yield, using the trifluoropyruvyl fluoride dimer obtained by the above method as a starting material.

DESCRIPTION OF EMBODIMENTS

The method of manufacturing a trifluoropyruvyl fluoride dimer (hereafter also referred to simply as "manufacturing method") according to one aspect of the present invention has a reaction step of reacting hexafluoropropylene oxide and aldehyde.

The above manufacturing method (hereafter also referred to as "dimer manufacturing method" or "dimer synthesis step") will be explained in further detail below.

Dimer Manufacturing Method (Dimer Synthesis Step)

In the dimer manufacturing method, aldehyde is used instead of the benzophenone that is used in the manufacturing method disclosed in PTL 1. As a result, the dimer manufacturing method can be carried out at a lower pressure than in the manufacturing method disclosed in PTL 1.

In one embodiment of the above manufacturing method, hexafluoropropylene oxide and aldehyde can be reacted at 0° C. to 100° C., preferably at 0° C. to 99° C., more preferably at 0° C. to 90° C., to generate an adduct of the aldehyde with hexafluoropropylene oxide, after which a reaction can be conducted at equal to or higher than 100° C., preferably at 100° C. to 200° C., and more preferably at 100° C. to 150° C. The above embodiment can be carried out, for example, at a pressure of equal to or lower than 1 MPa. Moreover, it becomes possible to manufacture a trifluoropyruvyl fluoride dimer with high yield.

In the above manufacturing method, in further detail, hexafluoropropylene oxide and aldehyde can be charged into a pressure-resistant vessel at equal to or lower than room temperature, and firstly a reaction can be conducted at 0° C. to 100° C., preferably at 0° C. to 99° C., and more preferably at 0° C. to 90° C., for 0.5 hour to 12.0 hours, to thereby generate an adduct of the aldehyde with hexafluoropropylene oxide, after which the temperature can be raised to equal to or higher than 100° C., preferably to 100° C. to 200° C., and more preferably to 100° C. to 150° C., and the reaction can be conducted for 5 hours to 48 hours. The reaction time can be shortened or extended as needed. The term room temperature denotes a temperature, for example, in the range of 20° C. to 25° C. In the reaction step of the above manufacturing method, specifically, hexafluoropropylene oxide and aldehyde are reacted at 0° C. to 100° C., preferably at 0° C. to 99° C., and more preferably at 0° C. to 90° C., for 0.5 hour to 12.0 hours. The above manufacturing method preferably has an aging step of, after the above reaction step, conducting a reaction at equal to or higher than 100° C., preferably at 100° C. to 200° C., and more preferably at 100° C. to 150° C., for 5 hours to 48 hours. Unless otherwise noted, the term temperature described in the disclosure of the present specification denotes the temperature of the reaction solution.

In the reaction step of causing hexafluoropropylene oxide and aldehyde to react, the aldehyde may be charged beforehand into a pressure-resistant vessel, whereupon the reaction may be conducted through continuous or intermittent addition of hexafluoropropylene oxide, over 0.5 hour to 24 hours.

Examples of the trifluoropyruvyl fluoride dimer include 4-fluoro-5-oxo-2,4-bis(trifluoromethyl)-1,3-dioxolane-2-carbonyl fluoride. Herein, 4-fluoro-5-oxo-2,4-bis(trifluoromethyl)-1,3-dioxolane-2-carbonyl fluoride can be represented by Formula A below.

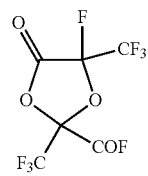

Formula A

The term aldehyde denotes herein one, two or more types of aldehyde. Specific examples of aldehyde include, for example, propionaldehyde, butyraldehyde, valeraldehyde, isovaleraldehyde, pivalaldehyde, 1-adamantane carbaldehyde, benzaldehyde, 2-methylbenzaldehyde, 3-methylbenzaldehyde, 4-methylbenzaldehyde, 2-ethylbenzaldehyde, 3-ethylbenzaldehyde, 4-ethylbenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2-bromobenzaldehyde, 3-bromobenzaldehyde, 4-bromobenzaldehyde, 1-naphthaldehyde, 5-methoxy-1-naphthaldehyde, 5-chloro-1-naphthaldehyde, 2-naphthaldehyde, 5-methoxy-2-naphthaldehyde, 5-chloro-2-naphthaldehyde and the like. Examples of preferred aldehyde include benzaldehyde, 2-methylbenzaldehyde, 3-methylbenzaldehyde, 4-methylbenzaldehyde, 2-ethylbenzaldehyde, 3-ethylbenzaldehyde, 4-ethylbenzaldehyde, 2-methoxybenzaldehyde, 3-methoxybenzaldehyde, 4-methoxybenzaldehyde, 2-ethoxybenzaldehyde, 3-ethoxybenzaldehyde and 4-ethoxybenzaldehyde. The aldehyde is preferably used in an amount of 0.8 mole to 1.2 moles with respect to the hexafluoropropylene oxide that is subjected to the reaction. For example, from the viewpoint of the yield of the trifluoropyruvyl fluoride dimer, aldehyde is preferred that has no hydrogen atom at the α-position of the carbonyl group. From the same viewpoint, aromatic aldehyde is preferably used as the aldehyde, more preferably electron donating group-substituted aromatic aldehyde, and yet more preferably electron donating group-substituted benzaldehyde.

The above reaction step can be carried out without a solvent, but solvents such as toluene, ethylbenzene, xylene, mesitylene, isopropylbenzene, anisole, chlorobenzene and the like may be used singly or in mixtures of two or more types in arbitrary proportions. In a case where a solvent is used, the amount thereof can be set to lie in the range of 0.1 times to 5.0 times the mass of the hexafluoropropylene oxide that is subjected to the reaction.

The reaction step is preferably carried out in a pressure-resistant vessel under conditions of equal to or lower than 3.5 MPa, more preferably equal to or lower than 1.2 MPa. The above pressure is the internal pressure within the vessel.

In the above reaction step, hexafluoropropylene oxide and aldehyde are allowed to react with each other, the adduct of the aldehyde with hexafluoropropylene oxide obtained in the reaction being also one aspect of the present invention.

The above aldehyde adduct can have a cyclized or linear structure depending on the manner in which the aldehyde is added to hexafluoropropylene oxide. Such aldehyde adduct can be represented by Formula 1, Formula 2 or Formula 3 below.

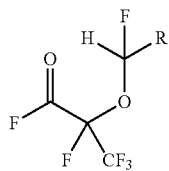

Formula 1

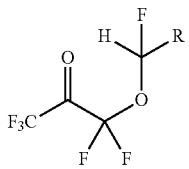

Formula 2

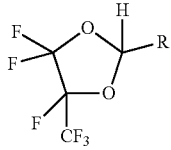

Formula 3

In Formulae 1 to 3 above, R represents a substituted or unsubstituted alkyl group or aryl group.

Method of Manufacturing perfluoro(2,4-dimethyl-2-fluoroformyl-1,3-dioxolane

Dimer Reaction Step

The above trifluoropyruvyl fluoride dimer can undergo a dimer reaction step in which the dimer reacts in the manner disclosed in the description of U.S. Pat. No. 3,308,107, and preferably an isomerization step, so that perfluoro(2,4-dimethyl-2-fluoroformyl-1,3-dioxolane) can be derived as a result.

In the dimer reaction step, the trifluoropyruvyl fluoride dimer and hexafluoropropylene oxide are allowed to react, in the presence of fluoride, in an organic solvent.

In one embodiment, the reaction solution obtained in the above dimer manufacturing method is cooled as needed down to about −20° C. to 30° C., whereby the reaction solution separates into two layers, namely an upper layer and a lower layer; then a layer (ordinarily the upper layer), made up of the mixture of byproducts (for example, a difluoromethyl compound, i.e. a fluorinated compound of the aldehyde) and/or a solvent, is separated and removed from the reaction solution; alternatively, the trifluoropyruvyl fluoride dimer may be purified as needed, for example, by distillation, to take part thereafter in the dimer reaction step.

In one embodiment, both the above upper layer and lower layer can be subjected to the dimer reaction step. As a result, it becomes possible to increase the yield of perfluoro(2,4-dimethyl-2-fluoroformyl-1,3-dioxolane) as compared with a case in which only the lower layer, being the layer that mainly can contain the trifluoropyruvyl fluoride dimer, is subjected to the dimer reaction step. That is, the present inventors conducted extensive research and newly found that the yield of perfluoro(2,4-dimethyl-2-fluoroformyl-1,3-dioxolane) can increase by performing the above dimer manufacturing method and the dimer reaction step in a so-called one-pot manner, without performing a process of separation of the target product from byproducts in the dimer manufacturing method. From the reaction solution that separates into two layers, namely an upper layer and a lower layer, and that is obtained by the above dimer manufacturing method, part of the upper layer and part of the lower layer may be extracted, separately or simultaneously; alternatively, the reaction solution having separated into two layers, namely the upper layer and the lower layer, and obtained by the above dimer manufacturing method, may be subjected to the dimer reaction step, as-is or by being mixed while under stirring.

The organic solvent used in the dimer reaction step is not particularly limited, so long as the organic solvent is inert towards the reaction. Examples of the organic solvent include, for example, aromatic solvents such as toluene, ethylbenzene, xylene and mesitylene, and ether-based solvents such as ethylene glycol dimethyl ether, diethylene glycol dimethyl ether, triethylene glycol dimethyl ether and tetraethylene glycol dimethyl ether. The organic solvent may be used singly; alternatively two or more types of organic solvents may be used in mixtures of arbitrary proportions. Organic solvents which are preferably used include, from the viewpoint of fluoride solubility, an ether-based solvent, such as ethylene glycol dimethyl ether, diethylene glycol dimethyl ether, triethylene glycol dimethyl ether, or tetraethylene glycol dimethyl ether, singly or in mixtures of two or more types in arbitrary proportions. The amount of organic solvent that is used in the reaction is not particularly limited, and ordinarily can be 0.3 times to 5.0 times the mass of the synthesis starting materials used in the reaction.

The fluoride used in the dimer reaction step is not particularly limited, so long as it is fluoride; specific examples thereof include alkali metal fluorides such as lithium fluoride, sodium fluoride, potassium fluoride and cesium fluoride; alkaline earth metal fluorides such as beryllium fluoride, magnesium fluoride, calcium fluoride, strontium fluoride and barium fluoride; and organic ammonium fluorides such as tetramethylammonium fluoride, tetraethylammonium fluoride, tetrapropylammonium fluoride, tetra-n-butylammonium fluoride and phenyltrimethylammonium fluoride. From the viewpoint of solubility in the organic solvent and reaction activity, one or more selected from the group consisting of sodium fluoride, potassium fluoride, cesium fluoride, tetramethylammonium fluoride, tetraethylammonium fluoride, tetrapropylammonium fluoride and tetra-n-butylammonium fluoride is preferably used as the fluoride. The fluoride can be used singly or in mixtures of two or more types in arbitrary proportions. The amount of fluoride used in the reaction can be set to lie, for example, in the range of 0.05 times to 1.00 time the molar amount of the trifluoropyruvyl fluoride dimer that is subjected to the reaction. The reaction is slow when the addition amount is excessively small, while the use of large amounts is uneconomical; accordingly, the amount of the fluoride that is used is preferably 0.1 times to 0.8 times by mole.

The amount of hexafluoropropylene oxide used in the dimer reaction step is preferably set to equal to or more than 2.00 times, more preferably to lie in the range of 2.05 times to 2.50 times, the molar amount of the trifluoropyruvyl fluoride dimer.

The order in which the various components are added to the reaction in the dimer reaction step is not particularly limited. It is preferable to prepare a mixture of a layer (ordinarily a lower layer) having mainly the trifluoropyruvyl fluoride dimer, in the reaction solution obtained by the above dimer manufacturing method, or both the upper layer and the lower layer, the fluoride and the organic solvent, and to add hexafluoropropylene oxide to the resulting mixture. For example, a mixture of both the upper layer and the lower layer of the reaction solution obtained by the above dimer manufacturing method, plus the fluoride and the organic solvent is prepared, the mixture being then adjusted to a temperature in the range of −20° C. to 60° C., followed by addition of hexafluoropropylene oxide over 0.5 hour to 48 hours. After addition of hexafluoropropylene oxide, in order to complete formation of perfluoro(3,5-dimethyl-2-oxo-1,4-dioxane), which is an intermediate for generating perfluoro (2,4-dimethyl-2-fluoroformyl-1,3-dioxolane), the temperature may be held in the above range for 2 hours to 24 hours. The dimer reaction step can be carried out preferably in a pressure-resistant vessel.

Isomerization Step

The dimer reaction step is preferably followed by an isomerization step. The isomerization step is a step of eliciting an isomerization reaction of perfluoro(3,5-dimethyl-2-oxo-1,4-dioxane) into perfluoro(2,4-dimethyl-2-fluoroformyl-1,3-dioxolane). Perfluoro(2,4-dimethyl-2-fluoroformyl-1,3-dioxolane) is represented by Formula 4, and may be obtained as a mixture of diastereomers.

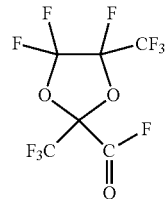

Formula 4

In the isomerization step, ordinarily the reaction solution after the dimer reaction step is heated at 100° C. to 150° C. for 4 hours to 48 hours, to allow the isomerization reaction to proceed to complete the isomerization. The isomerization step is preferably carried out within a pressure-resistant vessel. The pressure within the vessel in which the isomerization step is carried out is preferably set to lie in the range of 0.1 MPa to 1.0 MPa.

The isomerization step is followed, for example, by cooling down to room temperature and depressurization, with subsequent filtration and separation and removal of an organic solvent layer which is the upper layer, so that the target product perfluoro(2,4-dimethyl-2-fluoroformyl-1,3-dioxolane) can be obtained as a result.

The obtained perfluoro(2,4-dimethyl-2-fluoroformyl-1,3-dioxolane) can be hydrolyzed pursuant to Macromolecules 2005, 38, 4237-4245, to prepare a potassium salt thereof, after which perfluoro(2-methylene-4-methyl-1,3-dioxolane) can be derived through decarboxylation. Poly[perfluoro(2-methylene-4-methyl-1,3-dioxolane)] can then be obtained through polymerization of perfluoro(2-methylene-4-methyl-1,3-dioxolane). Poly[perfluoro(2-methylene-4-methyl-1,3-dioxolane)] is a polymer which is prospective, for example, as a resin for gas separation membranes and as a transparent resin for optical fibers.

EXAMPLES

The present invention will be further explained below by means of Examples. However, the present invention is not limited to the embodiments illustrated in Examples.

The following equipment was utilized in the analyses below.
$^{19}$F-NMR: AVANCE II 400, by Bruker
GC: GC-2025 (FID), by Shimadzu Corporation
GC-MS: GCMS-QP2010 (EI) by Shimadzu Corporation Example 1

Preparation of a Trifluoropyruvyl Fluoride Dimer

Butyraldehyde (1.37 kg, 19.00 mol) was charged into a 10 L autoclave made of SUS 316, having a pressure resistance of 8 MPa and equipped with a stirrer, and was cooled down to 0° C. on an ice bath, after which hexafluoropropylene oxide (3.15 kg, 18.97 mol) was added.

The autoclave was then sealed, followed by heating up to 60° C. while under stirring; this was held for 5 hours. Once the maximum pressure reached 0.9 MPa, the pressure dropped then to 0.06 MPa after 5 hours. The temperature was raised to 140° C., and that temperature was maintained for 8 hours. Once the maximum pressure reached 0.7 MPa, the pressure dropped then to 0.2 MPa after 8 hours.

Completion of the reaction was followed by cooling down to room temperature and subsequent separation, to yield a pale yellow transparent liquid (2.46 kg). A gas chromatograph and $^{19}$F-NMR analysis confirmed that the product was a trifluoropyruvic acid dimer alone. Quantification by $^{19}$F-NMR using benzotrifluoride as an internal standard substance revealed generation of 1.98 kg (6.87 mol) of the target trifluoropyruvic acid dimer (yield 72%/butyraldehyde basis). The above dimer was obtained as a 1/1 mixture (molar ratio) of two diastereomers.

$^{19}$F-NMR (neat, 376 MHz) (Isomer 1) δ22.40, −81.43, −81.82, −122.92, (Isomer 2) δ22.30, −81.69, −81.82, −122.10.

Example 2

Preparation of a Trifluoropyruvyl Fluoride Dimer

Using the same reaction apparatus as that of Example 1 but utilizing valeraldehyde (1.63 kg, 18.92 mol) instead of butyraldehyde (1.37 kg, 19.00 mol), herein hexafluoropropylene oxide (3.15 kg, 18.97 mol) was added, followed by holding at 70° C. for 3 hours, after which the reaction was conducted at 130° C. for 24 hours. The highest pressure at 70° C. and at 130° C. was 0.9 MPa and 0.6 MPa, respectively.

Completion of the reaction was followed by cooling down to room temperature and subsequent separation to yield a crude trifluoropyruvic acid dimer (pale yellow transparent liquid, 2.34 kg). Quantification by $^{19}$F-NMR using benzotrifluoride as an internal standard substance revealed generation of 1.98 kg (6.87 mol) of the target trifluoropyruvic acid dimer (yield 73%/valeraldehyde basis).

Example 3

Preparation of a Trifluoropyruvyl Fluoride Dimer

Using the same reaction apparatus as that of Example 1 but utilizing pivalaldehyde (1.63 kg, 18.92 mol) instead of butyraldehyde (1.37 kg, 19.00 mol), herein hexafluoropropylene oxide (3.15 kg, 18.97 mol) was added, followed by holding at 90° C. for 12 hours, after which the reaction was conducted at 140° C. for 36 hours. The highest pressure at 90° C. and 140° C. was 0.9 MPa and 0.7 MPa, respectively.

Completion of the reaction was followed by cooling down to room temperature and subsequent separation to yield a crude trifluoropyruvic acid dimer (pale yellow transparent liquid, 2.45 kg). Quantification by $^{19}$F-NMR using benzotrifluoride as an internal standard substance revealed generation of 2.13 kg (7.39 mol) of the target trifluoropyruvic acid dimer (yield 78%/pivalaldehyde basis).

Example 4

Preparation of a Trifluoropyruvyl Fluoride Dimer

Using the same reaction apparatus as that of Example 1 but utilizing benzaldehyde (2.01 kg, 18.94 mol) instead of butyraldehyde (1.37 kg, 19.00 mol), herein hexafluoropropylene oxide (3.15 kg, 18.97 mol) was added, followed by holding at 60° C. for 5 hours, after which the reaction was conducted at 130° C. for 8 hours. The highest pressure at 60° C. and at 130° C. was 0.7 MPa and 0.8 MPa, respectively.

Completion of the reaction was followed by cooling down to room temperature and subsequent separation to yield a crude trifluoropyruvic acid dimer (pale yellow transparent liquid, 2.56 kg). Quantification by $^{19}$F-NMR using benzotrifluoride as an internal standard substance revealed generation of 2.18 kg (7.57 mol) of the target trifluoropyruvic acid dimer (yield 80%/benzaldehyde basis).

Example 5

Preparation of a Trifluoropyruvyl Fluoride Dimer

Using the same reaction apparatus as that of Example 1 but utilizing 4-methoxybenzaldehyde (2.38 kg, 17.48 mol) instead of butyraldehyde (1.37 kg, 19.00 mol), herein hexafluoropropylene oxide (3.15 kg, 18.97 mol) was added, after which the reaction was conducted at 50° C. for 3 hours.

Part of the obtained reaction solution was removed, was isolated in accordance with a conventional method, and was analyzed quantitatively of several types of aldehyde adducts resulting from addition of the aldehyde to hexafluoropropylene oxide. The structures of the found aldehyde adducts 1 to 3 are given below.

(Aldehyde Adduct 1)

2,3,3,3-Tetrafluoro-2-[fluoro-(4-methoxy-phenyl)-methoxy]-propionyl fluoride

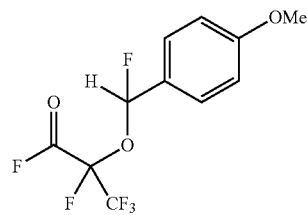 [SMILES: COc1ccc(C(F)OC(F)(C(=O)F)C(F)(F)F)cc1]

$^1$H-NMR (400 MHz, CDCl$_3$) δ 3.79 (3H), 6.68 (1H), 6.93 (2H), 7.40 (2H).

$^{19}$F-NMR (376 MHz, CDCl$_3$) δ 25.45, −82.60, −117.90, −136.07.

GC-MS (m/z): 302 (M$^+$), 139, 96, 69.

(Aldehyde Adduct 2)

1,1,1,3,3-Pentafluoro-3-[fluoro-(4-methoxy-phenyl)-methoxy]-propan-2-one

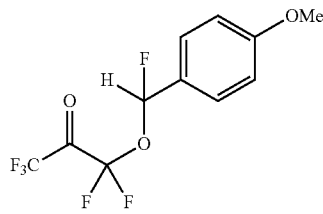 [SMILES: COc1ccc(C(F)OC(F)(F)C(=O)C(F)(F)F)cc1]

$^1$H-NMR (400 MHz, CDCl$_3$) δ 3.79 (3H), 6.38 (1H), 6.93 (2H), 7.40 (2H).

$^{19}$F-NMR (376 MHz, CDCl$_3$) δ −80.38, −83.53, −90.50, −120.04.

GC-MS (m/z): 302 (M$^+$), 139, 96, 69.

(Aldehyde Adduct 3)
4,4,5-Trifluoro-2-(4-methoxy-phenyl)-5-trifluoromethyl-[1,3]dioxolane

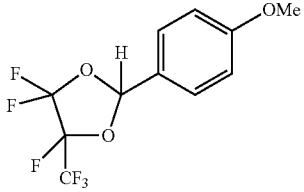 [SMILES: COc1ccc(C2OC(F)(F)C(F)(C(F)(F)F)O2)cc1]

$^1$H-NMR (400 MHz, CDCl$_3$) δ 3.79 (3H), 6.51 (1H), 6.93 (2H), 7.40 (2H).
$^{19}$F-NMR (376 MHz, CDCl$_3$) δ −79.65, −80.76, −86.38, −131.90.
GC-MS (m/z): 302 (M$^+$), 283, 271, 233, 167, 135, 120.

Next, the autoclave was sealed, and a reaction was carried out at 140° C. for 8 hours. The highest pressure at 50° C. and at 140° C. was 0.8 MPa and 0.6 MPa, respectively.

Completion of the reaction was followed by cooling down to room temperature and subsequent separation to yield a crude trifluoropyruvic acid dimer (pale yellow transparent liquid, 2.30 kg). Quantification by $^{19}$F-NMR using benzotrifluoride as an internal standard substance revealed generation of 2.15 kg (7.46 mol) of the target trifluoropyruvic acid dimer (yield 85%/4-methoxybenzaldehyde basis).

Example 6

Preparation of a Trifluoropyruvyl Fluoride Dimer

Using the same reaction apparatus as that of Example 1 but utilizing 4-methylbenzaldehyde (2.10 kg, 17.48 mol) instead of butyraldehyde (1.37 kg, 19.00 mol), hexafluoropropylene oxide (2.91 kg, 17.53 mol) was added, followed by holding at 70° C. for 3 hours, after which the reaction was conducted at 130° C. for 6 hours. The highest pressure at 70° C. and at 130° C. was 0.9 MPa and 0.7 MPa, respectively.

Completion of the reaction was followed by cooling down to room temperature and subsequent separation to yield a crude trifluoropyruvic acid dimer (pale yellow transparent liquid, 2.24 kg). Quantification by $^{19}$F-NMR using benzotrifluoride as an internal standard substance revealed generation of 2.09 kg (7.26 mol) of the target trifluoropyruvic acid dimer (yield 83%/4-methylbenzaldehyde basis).

Example 7

Preparation of a Trifluoropyruvyl Fluoride Dimer

Using the same reaction apparatus as that of Example 1 but utilizing 2-methoxybenzaldehyde (2.38 kg, 17.48 mol) instead of butyraldehyde (1.37 kg, 19.00 mol), hexafluoropropylene oxide (3.48 kg, 20.96 mol) was added, followed by holding at 70° C. for 6 hours, after which the reaction was conducted at 150° C. for 6 hours. The highest pressure at 70° C. and at 150° C. was 0.8 MPa and 0.6 MPa, respectively.

Completion of the reaction was followed by cooling down to room temperature and subsequent separation to yield a crude trifluoropyruvic acid dimer (pale yellow transparent liquid, 2.20 kg). Quantification by $^{19}$F-NMR using benzotrifluoride as an internal standard substance revealed generation of 2.04 kg (7.08 mol) of the target trifluoropyruvic acid dimer (yield 81%/2-methoxybenzaldehyde basis).

Example 8

Preparation of a Trifluoropyruvyl Fluoride Dimer

Using the same reaction apparatus as that of Example 1 but utilizing 2-methylbenzaldehyde (2.10 kg, 17.48 mol) instead of butyraldehyde (1.37 kg, 19.00 mol), hexafluoropropylene oxide (2.91 kg, 17.53 mol) was added, followed by holding at 70° C. for 5 hours, after which the reaction was conducted at 140° C. for 12 hours. The highest pressure at 70° C. and at 140° C. was 0.9 MPa and 0.6 MPa, respectively.

Completion of the reaction was followed by cooling down to room temperature and subsequent separation to yield a crude trifluoropyruvic acid dimer (pale yellow transparent liquid, 2.23 kg). Quantification by $^{19}$F-NMR using benzotrifluoride as an internal standard substance revealed generation of 2.02 kg (7.01 mol) of the target trifluoropyruvic acid dimer (yield 80%/2-methylbenzaldehyde basis).

Example 9

Preparation of a Trifluoropyruvyl Fluoride Dimer

Using the same reaction apparatus as that of Example 1, 4-methoxybenzaldehyde (2.38 kg, 17.48 mol), hexafluoropropylene oxide (3.15 kg, 18.97 mol) and anisole (2.0 kg, 18.49 mol) were charged, and the reaction was conducted at 50° C. for 10 hours, after which the reaction was conducted at 140° C. for 24 hours. The highest pressure at 50° C. and at 140° C. was 0.6 MPa and 0.4 MPa, respectively.

Completion of the reaction was followed by cooling down to room temperature and subsequent separation to yield a crude trifluoropyruvic acid dimer (pale yellow transparent liquid, 2.03 kg). Quantification by $^{19}$F-NMR using benzotrifluoride as an internal standard substance revealed generation of 1.84 kg (6.39 mol) of the target trifluoropyruvic acid dimer (yield 73%/4-methoxybenzaldehyde basis).

Example 10

Preparation of a Trifluoropyruvyl Fluoride Dimer

Using the same reaction apparatus as that of Example 1, 4-methoxybenzaldehyde (2.38 kg, 17.48 mol), hexafluoropropylene oxide (3.15 kg, 18.97 mol) and toluene (2.50 kg, 27.13 mol) were charged, and the reaction was conducted at 60° C. for 8 hours, after which the reaction was conducted at 140° C. for 30 hours. The highest pressure at 60° C. and at 140° C. was 0.4 MPa and 0.6 MPa, respectively.

Completion of the reaction was followed by cooling down to room temperature and subsequent separation to yield a crude trifluoropyruvic acid dimer (pale yellow transparent liquid, 2.06 kg). Quantification by $^{19}$F-NMR using benzotrifluoride as an internal standard substance revealed generation of 1.92 kg (6.67 mol) of the target trifluoropyruvic acid dimer (yield 76%/4-methoxybenzaldehyde basis).

Example 11

Preparation of a Trifluoropyruvyl Fluoride Dimer

Using the same reaction apparatus as that of Example 1, 4-methoxybenzaldehyde (2.38 kg, 17.48 mol), hexafluoropropylene oxide (3.15 kg, 18.97 mol) and mesitylene (1.4 kg, 11.65 mol) were charged and the reaction was conducted at 50° C. for 6 hours, after which the reaction was conducted at 140° C. for 18 hours. The highest pressure at 50° C. and at 140° C. was 0.7 MPa and 0.5 MPa, respectively.

Completion of the reaction was followed by cooling down to room temperature and subsequent separation to yield a crude trifluoropyruvic acid dimer (pale yellow transparent liquid, 2.00 kg). Quantification by $^{19}$F-NMR using benzotrifluoride as an internal standard substance revealed generation of 1.77 kg (6.14 mol) of the target trifluoropyruvic acid dimer (yield 70%/4-methoxybenzaldehyde basis).

Example 12

Preparation of a Trifluoropyruvyl Fluoride Dimer

Using the same reaction apparatus as that of Example 1, 4-methoxybenzaldehyde (2.38 kg, 17.48 mol), hexafluoropropylene oxide (3.15 kg, 18.97 mol) and chlorobenzene (0.6 kg, 5.33 mol) were charged, and the reaction was conducted at 60° C. for 5 hours, after which the reaction was conducted at 140° C. for 10 hours. The highest pressure at 60° C. and at 140° C. was 0.5 MPa and 0.6 MPa, respectively.

Completion of the reaction was followed by cooling down to room temperature and subsequent separation to yield a crude trifluoropyruvic acid dimer (pale yellow transparent liquid, 1.98 kg). Quantification by $^{19}$F-NMR using benzotrifluoride as an internal standard substance revealed generation of 1.71 kg (5.94 mol) of the target trifluoropyruvic acid dimer (yield 68%/4-methoxybenzaldehyde basis).

Example 13

Preparation of a Trifluoropyruvyl Fluoride Dimer

Using the same reaction apparatus as that of Example 1, 4-methoxybenzaldehyde (1.19 kg, 8.74 mol), hexafluoropropylene oxide (1.58 kg, 9.52 mol) and anisole (4.0 kg, 36.99 mol), were charged and the reaction was conducted at 70° C. for 12 hours, after which the reaction was conducted at 140° C. for 48 hours. The highest pressure at 70° C. and at 140° C. was 0.7 MPa and 0.7 MPa, respectively.

Completion of the reaction was followed by cooling down to room temperature and subsequent separation to yield a crude trifluoropyruvic acid dimer (pale yellow transparent liquid, 1.09 kg). Quantification by $^{19}$F-NMR using benzotrifluoride as an internal standard substance revealed generation of 0.93 kg (3.23 mol) of the target trifluoropyruvic acid dimer (yield 74%/4-methoxybenzaldehyde basis).

Example 14

Preparation of a Trifluoropyruvyl Fluoride Dimer

Using the same reaction apparatus as that of Example 1, 4-methoxybenzaldehyde (2.38 kg, 17.48 mol) and hexafluoropropylene oxide (3.15 kg, 18.97 mol) were charged, and the reaction was conducted at 140° C. for 12 hours. The highest pressure during this time was 1.7 MPa.

Completion of the reaction was followed by cooling down to room temperature and subsequent separation to yield a crude trifluoropyruvic acid dimer (pale yellow transparent liquid, 1.98 kg). Quantification by $^{19}$F-NMR using benzotrifluoride as an internal standard substance revealed generation of 1.81 kg (6.28 mol) of the target trifluoropyruvic acid dimer (yield 72%/4-methoxybenzaldehyde basis).

Example 15

Preparation of a Trifluoropyruvyl Fluoride Dimer

Using the same reaction apparatus as that of Example 1, 4-methoxybenzaldehyde (2.38 kg, 17.48 mol) was charged, with heating up to 85° C., after which hexafluoropropylene oxide (3.15 kg, 18.97 mol) was continuously supplied over 7 hours while maintaining that temperature, to carry out a reaction step. The pressure at this time exhibited a maximum of 0.2 MPa. The reaction was then conducted for 12 hours at 140° C. as the reaction temperature. The highest pressure at 140° C. was 0.7 MPa.

Completion of the reaction was followed by cooling down to room temperature and subsequent separation to yield a crude trifluoropyruvic acid dimer (pale yellow transparent liquid, 2.35 kg). Quantification by $^{19}$F-NMR using benzotrifluoride as an internal standard substance revealed generation of 2.17 kg (7.53 mol) of the target trifluoropyruvic acid dimer (yield 86%/4-methoxybenzaldehyde basis).

Example 16

Preparation of a Trifluoropyruvyl Fluoride Dimer

Using the same reaction apparatus as that of Example 1, 4-methoxybenzaldehyde (2.38 kg, 17.48 mol) and toluene (2.50 kg, 27.13 mol) were charged, with heating up to 85° C., after which hexafluoropropylene oxide (3.15 kg, 18.97 mol) was continuously supplied over 8 hours while maintaining that temperature, to carry out a reaction step. The pressure at this time exhibited a maximum of 0.2 MPa. The reaction was then conducted for 30 hours at 140° C. as the reaction temperature. The highest pressure at 140° C. was 0.6 MPa.

Completion of the reaction was followed by cooling down to room temperature and subsequent separation to yield a crude trifluoropyruvic acid dimer (pale yellow transparent liquid, 2.21 kg). Quantification by $^{19}$F-NMR using benzotrifluoride as an internal standard substance revealed generation of 1.94 kg (6.73 mol) of the target trifluoropyruvic acid dimer (yield 77%/4-methoxybenzaldehyde basis).

Example 17

Preparation of a Trifluoropyruvyl Fluoride Dimer

Using the same reaction apparatus as that of Example 1 but utilizing 4-methoxybenzaldehyde (2.38 kg, 17.48 mol) instead of butyraldehyde (1.37 kg, 19.00 mol), hexafluoropropylene oxide (3.15 kg, 18.97 mol) was added, after which the reaction was conducted at 50° C. for 3 hours, and then at 180° C. for 2 hours. The highest pressure at 50° C. and at 180° C. was 0.8 MPa and 1.9 MPa, respectively.

Completion of the reaction was followed by cooling down to room temperature and subsequent separation to yield a crude trifluoropyruvic acid dimer (pale yellow transparent liquid, 2.34 kg). Quantification by $^{19}$F-NMR using benzotrifluoride as an internal standard substance revealed generation of 2.11 kg (7.33 mol) of the target trifluoropyruvic acid dimer (yield 84%/4-methoxybenzaldehyde basis).

Example 18

Preparation of perfluoro(2,4-dimethyl-2-fluoro-formyl-1,3-dioxolane)

The trifluoropyruvic acid dimer (123.18 g, pure content 99.15 g, 0.344 mol) prepared in Example 1, cesium fluoride (15.78 g, 0.104 mol) and diglyme (66.94 g, 0.499 mol) were charged into a 1 L autoclave made of SUS 316, having a pressure resistance of 8 MPa and equipped with a stirrer, and cooled down to 0° C. on an ice bath. Then, hexafluoropropylene oxide (114.22 g, 0.688 mol) was added thereto over 2 hours, followed by heating to 120° C., with the reaction being conducted for 24 hours.

Completion of the reaction was followed by cooling down to room temperature, and separation to yield crude perfluoro (2,4-dimethyl-2-fluoroformyl-1,3-dioxolane) (yellow liquid, 168.46 g). Quantification by $^{19}$F-NMR using benzotrifluoride as an internal standard substance revealed generation of 145.22 g (0.468 mol) of the target perfluoro(2,4-dimethyl-2-fluoroformyl-1,3-dioxolane) (yield 68%/trifluoropyruvic acid dimer basis). The above target product was obtained as a 6/4 (molar ratio) mixture of two diastereomers.

$^{19}$F-NMR (neat, 376 MHz) (Isomer 1) δ23.63, −77.76 (d, J=131.6 Hz), −80.13, −81.57, −83.56 (d, J=135.4 Hz), −124.91. (Isomer 2) δ23.16, −78.45 (d, J=131.6 Hz), −80.37, −81.56, −84.05 (d, J=139.1 Hz), −123.72.

Comparative Example 1

Preparation of a Trifluoropyruvyl Fluoride Dimer

Benzophenone (3.19 kg, 17.51 mol) was charged into a 10 L autoclave made of SUS 316, having a pressure resistance of 8 MPa and equipped with a stirrer, and was cooled down to 0° C. in an ice bath, followed by addition of hexafluoropropylene oxide (3.15 kg, 18.97 mol).

The autoclave was then sealed, followed by heating up to 185° C. while under stirring, and the reaction was conducted for 4 hours. Once the maximum pressure reached 4.7 MPa, the pressure dropped then to 3.5 MPa; however, the reaction proceeded at a higher pressure than in the above Examples.

Completion of the reaction was followed by cooling down to room temperature and subsequent separation to yield a crude trifluoropyruvic acid dimer (pale yellow transparent liquid, 2.06 kg). Quantification by $^{19}$F-NMR using benzotrifluoride as an internal standard substance revealed generation of 1.82 kg (6.32 mol) of the target trifluoropyruvic acid dimer (yield 72%/benzophenone basis).

Example 19

Confirmation of the Product in the Dimer Synthesis Step

Herein 4-methoxybenzaldehyde (91.6 g, 0.673 mol) was charged into a 500 mL autoclave made of SUS 316, having a pressure resistance of 8 MPa and equipped with a stirrer, and the whole was cooled down to 0° C. on an ice bath, followed by addition of hexafluoropropylene oxide (115.1 g, 0.693 mol).

Next, the autoclave was sealed, and was thereafter heated at 55° C. for 3 hours while under stirring, followed by heating up to 150° C., whereupon the reaction was conducted for 8 hours. The highest pressure during this time was 0.9 MPa.

Completion of the reaction was followed by cooling down to 0° C., whereupon an upper layer (brown, 114.3 g) and lower layer (pale yellow, 88.1 g) that had separated were each quantitatively analyzed by $^{19}$F-NMR using benzotrifluoride as an internal standard substance. The results revealed that the upper layer contained 8.0 g (0.0278 mol, yield 8%, 4-methoxybenzaldehyde basis) and the lower layer contained 81.5 g (0.283 mol, yield 84%, 4-methoxybenzaldehyde basis) of the target trifluoropyruvyl fluoride dimer. The main component of the upper layer was a fluorinated product of 4-methoxybenzaldehyde, given below.

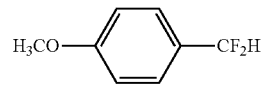 [SMILES: COc1ccc(C(F)F)cc1]

<Dimer Synthesis Step, Dimer Reaction Step and Isomerization Step>

Herein 4-methoxybenzaldehyde (91.6 g, 0.673 mol) was charged into a 500 mL autoclave made of SUS 316, having a pressure resistance of 8 MPa and equipped with a stirrer, and the whole was cooled down to 0° C. on an ice bath, followed by addition of hexafluoropropylene oxide (115.1 g, 0.693 mol).

Next, the autoclave was sealed, and was thereafter heated at 55° C. for 3 hours while under stirring, followed by heating up to 150° C., whereupon the reaction was conducted for 8 hours. The highest pressure during this time was 0.9 MPa.

Completion of the reaction was followed by cooling down to 0° C., to obtain a reaction solution that separated into two layers, namely an upper layer and a lower layer. Next, cesium fluoride (14.2 g, 0.0935 mol) and diethylene glycol dimethyl ether (141.5 g, 1.05 mol) were added to the obtained reaction solution (liquid weight 202.4 g (total trifluoropyruvic acid dimer 89.5 g, 0.311 mol)), in the autoclave, with cooling down to 0° C. on an ice bath. Then, hexafluoropropylene oxide (108.3 g, 0.652 mol) was added thereto over 6 hours. The temperature was held throughout at 0° C. to 10° C. After aging by holding of the above temperature range for 4 hours, the autoclave was heated again up to 130° C., and an isomerization reaction was conducted for 24 hours.

Completion of the reaction was followed by cooling down to room temperature, and separation to yield crude perfluoro (2,4-dimethyl-2-fluoroformyl-1,3-dioxolane) (pale yellow liquid, 157.8 g). Quantification by $^{19}$F-NMR using benzotrifluoride as an internal standard substance revealed generation of 130.6 g (0.421 mol) of the target perfluoro(2,4-dimethyl-2-fluoroformyl-1,3-dioxolane) (yield 63%, 4-methoxybenzaldehyde basis). The obtained target product was a mixture of two diastereomers, at a ratio of 6/4 (molar ratio).

$^{19}$F-NMR (neat, 376 MHz) (Isomer 1) δ 23.63, −77.76 (d, J=131.6 Hz), −80.13, −81.57, −83.56 (d, J=135.4 Hz), −124.91. (Isomer 2) δ23.16, −78.45 (d, J=131.6 Hz), −80.37, −81.56, −84.05 (d, J=139.1 Hz), −123.72.

Example 20

The same operation as in Example 19 was carried out using the same apparatus as in Example 19, to perform a dimer synthesis step, a dimer reaction step and an isomerization step. Herein, however, a layer separation operation was carried out after the dimer synthesis reaction, to remove the upper layer of the reaction solution, whereupon the dimer reaction step and the isomerization step were carried out using the lower layer alone. Completion of the isomerization step was followed by cooling down to room temperature, and separation to yield crude perfluoro(2,4-dimethyl-2-fluoroformyl-1,3-dioxolane) (pale yellow liquid, 136.3 g). Quantification by $^{19}$F-NMR using benzotrifluoride as an internal standard substance revealed generation of 109.3 g (0.353 mol) of the target perfluoro(2,4-dimethyl-2-fluoroformyl-1,3-dioxolane) (yield 52%, 4-methoxybenzaldehyde basis).

The above results reveal that a higher yield of perfluoro (2,4-dimethyl-2-fluoroformyl-1,3-dioxolane) could be achieved in Example 19, where both the upper layer and the lower layer of the reaction solution were subjected to the dimer reaction step, without any layer separation operation after the dimer synthesis step, as compared with Example 20.

Example 21

<Confirmation of the Product in the Dimer Synthesis Step>

Herein 4-methoxybenzaldehyde (91.6 g, 0.673 mol) and toluene (45.8 g, 0.497 mol) were charged into a 500 mL autoclave made of SUS 316, having a pressure resistance of 8 MPa and equipped with a stirrer, with cooling down to 0° C. on an ice bath, followed by addition of hexafluoropropylene oxide (115.1 g, 0.693 mol).

Next, the autoclave was sealed, and was thereafter heated at 55° C. for 3 hours while under stirring, followed by heating up to 150° C., whereupon the reaction was conducted for 8 hours. The highest pressure during this time was 0.9 MPa.

Completion of the reaction was followed by cooling down to 0° C., whereupon an upper layer (brown, 159.8 g) and lower layer (pale yellow, 83.4 g) that had separated were each quantitatively analyzed by $^{19}$F-NMR using benzotrifluoride as an internal standard substance. The results revealed that the upper layer contained 14.6 g (0.0507 mol, yield 15%, 4-methoxybenzaldehyde basis) and the lower layer contained 72.6 g (0.252 mol, yield 75%, 4-methoxybenzaldehyde basis) of the target trifluoropyruvyl fluoride dimer. The main component of the upper layer was toluene and a fluorinated product of 4-methoxybenzaldehyde.

<Dimer Synthesis Step, Dimer Reaction Step and Isomerization Step>

Herein 4-methoxybenzaldehyde (91.6 g, 0.673 mol) and toluene (45.8 g, 0.497 mol) were charged into a 500 mL autoclave made of SUS 316, having a pressure resistance of 8 MPa and equipped with a stirrer, and the whole was cooled down to 0° C. on an ice bath, followed by addition of hexafluoropropylene oxide (115.1 g, 0.693 mol).

Next, the autoclave was sealed, and was thereafter heated at 55° C. for 3 hours while under stirring, followed by heating up to 150° C., whereupon the reaction was conducted for 8 hours. The highest pressure during this time was 0.9 MPa.

Completion of the reaction was followed by cooling down to 0° C., to obtain a reaction solution that separated into two layers, namely an upper layer and a lower layer. Next, cesium fluoride (11.5 g, 0.0757 mol) and diethylene glycol dimethyl ether (115.0 g, 0.857 mol) were added to the obtained reaction solution (liquid weight 243.2 g (total trifluoropyruvic acid dimer 87.2 g, 0.303 mol)), in the autoclave, with cooling down to 0° C. on an ice bath. Then, hexafluoropropylene oxide (105.6 g, 0.636 mol) was added thereto over 6 hours. The temperature was held throughout at 0° C. to 10° C. After aging by holding of the above temperature range for 4 hours, the autoclave was heated again up to 130° C., and an isomerization reaction was conducted for 24 hours.

Completion of the reaction was followed by cooling down to room temperature, and separation to yield crude perfluoro (2,4-dimethyl-2-fluoroformyl-1,3-dioxolane) (pale yellow liquid, 155.7 g). Quantification by $^{19}$F-NMR using benzotrifluoride as an internal standard substance revealed generation of 129.0 g (0.416 mol) of the target perfluoro(2,4-dimethyl-2-fluoroformyl-1,3-dioxolane) (yield 62%, 4-methoxybenzaldehyde basis).

Example 22

The same operation as in Example 21 was carried out using the same apparatus as in Example 21, to perform a dimer synthesis step, a dimer reaction step and an isomerization step. Herein, however, a layer separation operation was carried out after the dimer synthesis reaction, to remove the upper layer of the reaction solution, whereupon the dimer reaction step and the isomerization step were carried out using the lower layer alone. Completion of the isomerization step was followed by cooling down to room temperature, and separation to yield crude perfluoro(2,4-dimethyl-2-fluoroformyl-1,3-dioxolane) (pale yellow liquid, 122.2 g). Quantification by $^{19}$F-NMR using benzotrifluoride as an internal standard substance revealed generation of 98.7 g (0.318 mol) of the target perfluoro(2,4-dimethyl-2-fluoroformyl-1,3-dioxolane) (yield 47%, 4-methoxybenzaldehyde basis).

The above results reveal that a higher yield of perfluoro (2,4-dimethyl-2-fluoroformyl-1,3-dioxolane) could be achieved in Example 21, where both the upper layer and the lower layer of the reaction solution were subjected to the dimer reaction step, without any layer separation operation after the dimer synthesis step, as compared with Example 22.

According to one aspect of the present invention, a trifluoropyruvyl fluoride dimer can be manufactured on an industrial scale. The trifluoropyruvyl fluoride dimer obtained by the above manufacturing method can be derived into perfluoro(2,4-dimethyl-2-fluoroformyl-1,3-dioxolane); in turn, this perfluoro(2,4-dimethyl-2-fluoroformyl-1,3-dioxolane) can be used as a synthesis starting material of poly[perfluoro(2-methylene-4-methyl-1,3-dioxolane)], which is a polymer, being prospective, for example, as a resin for gas separation membranes and as a transparent resin for optical fibers.

The invention claimed is:

1. A method of manufacturing a trifluoropyruvyl fluoride dimer the method comprising:
    reacting hexafluoropropylene oxide and aldehyde at a temperature of from 0° C. to 99° C. for 0.5 hour to 12.0 hours, thereby generating an adduct of the aldehyde with the hexafluoropropylene oxide, and then
    aging a reaction product of the hexafluoropropylene oxide and the aldehyde at a temperature of from 100° C. to 150° C. for 5 hours to 48 hours, after the reacting,
    wherein the aldehyde is at least one aldehyde selected from the group consisting of butyraldehyde, valeraldehyde, pivaldehyde, 4-methoxybenzaldehyde, and 2-methoxybenzaldehyde.

2. The method of claim 1, wherein the aldehyde is 4-methoxybenzaldehyde.

3. The method of claim 1, wherein the reacting is carried out at 3.5 MPa or lower.

4. A method of manufacturing perfluoro(2,4-dimethyl-2-fluoroformyl-1,3-dioxolane), the method comprising:
   synthesizing a trifluoropyruvyl fluoride dimer by the method according to claim 1; and
   reacting the synthesized trifluoropyruvyl fluoride dimer.

5. The method of claim 4,
   wherein the reacting comprises a reaction of the trifluoropyruvyl fluoride dimer and hexafluoropropylene oxide in the presence of a fluoride, in an organic solvent.

6. The method of claim 4, further comprising an isomerization after the reacting the synthesized trifluoropyruvyl fluoride dimer.

7. The method of claim 1, wherein the aldehyde is butyraldehyde.

8. The method of claim 1, wherein the aldehyde is valeraldehyde pivaldehyde.

9. The method of claim 1, wherein the aldehyde is 2-methoxybenzaldehyde.

\* \* \* \* \*